United States Patent [19]

Blum et al.

[11] 4,125,608

[45] Nov. 14, 1978

[54] APPETITE CURBING PREPARATION CONTAINING AN ALGINATE AND A DIPHOSPHONIC ACID

[75] Inventors: Helmut Blum, Düsseldorf-Holthausen; Christian Gloxhuber, Haan; Christian Heine, Monheim, Rhld.; Karl-Heinz Worms, Düsseldorf-Holthausen, all of Fed. Rep. of Germany

[73] Assignee: Henkel Kommanditgesellschaft Auf Aktien (Henkel KGaA), Dusseldorf, Fed. Rep. of Germany

[21] Appl. No.: 740,531

[22] Filed: Nov. 10, 1976

Related U.S. Application Data

[63] Continuation-in-part of Ser. No. 555,062, Mar. 3, 1975, abandoned.

[30] Foreign Application Priority Data

Mar. 16, 1974 [DE] Fed. Rep. of Germany ....... 2412827

[51] Int. Cl.$^2$ .................... A01N 9/00; A01N 9/28; A01N 9/36
[52] U.S. Cl. .................................. 424/180; 424/204
[58] Field of Search ................................ 424/204, 180

[56] References Cited

U.S. PATENT DOCUMENTS

| | | | |
|---|---|---|---|
| 2,935,447 | 5/1960 | Miller et al. | 424/180 |
| 3,683,080 | 8/1972 | Francis | 424/204 |
| 3,843,786 | 10/1974 | Wong | 424/180 |

OTHER PUBLICATIONS

Heim; Handbook of Non-Prescription Drugs, (1973), pp. 94–98.
Fleisch et al., Europ. J. Clinical Invest., 1, pp. 12–18 (1970).
Kirk–Othmer, Encyclopedia of Chem. Tech. 2nd ed., vol. 6, p. 802 (1965).
Osol et al., The Dispensatory of the United States of America, 25th ed., pp. 1250–1251 (1955).

*Primary Examiner*—Albert T. Meyers
*Assistant Examiner*—D. W. Robinson
*Attorney, Agent, or Firm*—Hammond & Littell

[57] ABSTRACT

An appetite curbing preparation comprising an alginate and diphosphonic acid or a nontoxic pharmacologically acceptable water-soluble salt thereof as an inhibitor of the precipitation of calcium salts. This preparation is useful for curbing the appetite of a warm-blooded animal.

12 Claims, No Drawings

APPETITE CURBING PREPARATION CONTAINING AN ALGINATE AND A DIPHOSPHONIC ACID

CROSS-REFERENCE TO RELATED APPLICATION

This is a continuation-in-part of our application Ser. No. 555,062 filed on Mar. 3, 1975, now abandoned.

FIELD OF THE INVENTION

The present invention relates to appetite curbing compositions for mammals, methods for the preparation of such compositions, and methods for curbing the appetite of mammals by use of said compositions.

BACKGROUND OF THE INVENTION

It is known to produce preparations based on alginates for use as appetite curbing agents in slimming diets. Since these preparations swell in the stomach and intestinal tract, they produce a feeling of fullness and satisfaction in human beings. However, the preparations have a considerable disadvantage in that in the presence of calcium ions they form calcium-containing deposits of low solubility. As a result, it is possible for a calcium ion deficiency to be produced, particularly in the intestinal tract. The fear has therefore often been voiced that disturbances of the metabolism could thereby be produced.

OBJECTS OF THE INVENTION

It is an object of the present invention to overcome the above-described drawbacks of the prior art.

It is another object of the present invention to provide a preparation comprising alginic acid and a diphosphonic acid (or nontoxic pharmacologically acceptable water-soluble salts thereof) in which the diphosphonic acid acts as inhibitor of the precipitation of calcium salts; and thereby inhibits precipitation of calcium ions; this preparation is useful for curbing the appetite of a warm-blooded animal.

These and further objects of the present invention will become apparent as the description thereof proceeds.

DESCRIPTION OF THE INVENTION

The present invention relates to alginic acid preparations containing a diphosphonic acid (or nontoxic pharmacologically acceptable water-soluble salts thereof) as inhibitor of the precipitation of calcium salts when the composition is ingested. This preparation is useful as an appetite curbing agent for warm-blooded animals.

Accordingly, the present invention provides a preparation for use in curbing the appetite of warm-blooded animals which comprises an alginic compound and a diphosphonic compound of the formula:

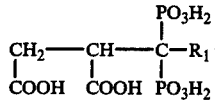

wherein $R_1$ is hydrogen or methyl and the nontoxic pharmacologically acceptable water-soluble salts thereof, as inhibitor of the precipitation of calcium salts when the composition is administered to warm-blooded animals.

More particularly, the present invention is directed to an appetite curbing preparation for warm-blooded animals comprising (A) an alginic compound selected from the group consisting of alginic acid and the nontoxic pharmacologically acceptable water-soluble salts thereof, and (B) a substoichiometric amount based on the calcium ions required to gel said alginic compound of a diphosphonic compound as precipitation inhibitor for calcium ions selected from the group consisting of a diphosphonic compound having the formula

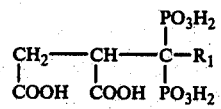

wherein $R_1$ is hydrogen or methyl and the nontoxic pharmacologically acceptable water-soluble salts thereof.

Also, the present invention provides an appetite curbing composition for a warm-blooded animal consisting essentially of 25% to 50% by weight of the above appetite curbing preparation and 50% to 75% by weight of a nontoxic pharmacologically acceptable carrier.

In addition, the present invention provides a method for curbing the appetite of warm-blooded animals comprising administering to said animals an anoretically effective amount of the appetite curbing preparation mentioned above.

Also, the present invention provides an improvement in a process for dieting, which consists essentially in consuming (during or before a meal) an effective amount of the appetite curbing preparation mentioned above as an anoretic material.

It has become apparent that in principle it is possible to prevent the formation of calcium alginate by adding thereto a strong sequestering agent, for example, nitrilotriacetic acid or ethylenediaminetetraacetic acid. However, the calcium ions are thereby sequestered to such an extent that they may possibly no longer be available for physiological processes in the warm-blooded animal. Moreover, the precipitation of the calcium salts can be prevented for a considerable period of time by using compounds which have a strong inhibiting effect (threshold effect). In this case, crystalline growth is probably inhibited to a very great extent by the incorporation of the inhibitor into seed crystals. Compounds having a threshold effect particularly include polyphosphates having a chain-like structure and include sequestering agent phosphonic acids, such as methylphosphonosuccinic acid or 2-phosphonobutane-1,2,4-tricarboxylic acid. However, condensed phosphates are not suitable for this purpose since they are split up by phosphatases in the body to give ineffective monophosphate. Moreover, tests have shown that, under the physiological conditions which prevail in the intestinal tract, the majority of sequestering agent phosphonic acids are either unsuitable or are not sufficiently effective.

It was therefore surprising that the above-mentioned dicarboxy diphosphonic acids and their nontoxic pharmacologically acceptable water-soluble salts constitute suitable ingredients for the above preparation. The compounds are diphosphonoalkanedicarboxylic acids selected from the group consisting of 1,1-diphosphonopropane-2,3-dicarboxylic acid and 2,2-diphosphonobutane-3,4-dicarboxylic acid, with the former acid being preferred.

Instead of these acids, it is also possible to use their nontoxic pharmacologically acceptable, water-soluble salts, such as the alkali metal salts, for example, sodium and potassium, and the magnesium salts, and the ammonium and substituted ammonium salts such as the lower alkylolammonium salts, for example, the mono-, di- or triethylolammonium salts. It is also possible to use the partial salts, in which only a proportion of the acidic protons is replaced by other cations. Partial salts, which produce a pH in the range from 6 to 8.5 in aqueous solution, are preferred. Mixtures of the above-mentioned acids and their salts can also be used.

The proportion of the precipitation inhibitors in the appetite curbing preparations containing an alginic compound is variable. However, this proportion must be great enough to inhibit the precipitation of calcium ions in the intestinal tract. This precipitation is possibly caused by the presence of calcium hardness (i.e., calcium ions) in the water. Based upon a 10 gm amount of the alginic compound, about 50 to 200 mg, preferably 100 to 200 mg, of the precipitation inhibitor can be present in compositions of the invention. This corresponds to the weight ratio of (50 to 200):1 for the alginic compound to the precipitation inhibitor, equivalent to ½% to 2% of the inhibitor on the weight of the alginic compound. However, for the reasons as stated above, precipitation inhibitor is preferably present in substoichiometric amount based on the calcium required to gel said alginic compound.

Commercial alginic acid, or its nontoxic pharmacologically acceptable water-soluble salts such as the alkali metal salts, are suitable as the alginic ingredient. Potassium alginate or, preferably, sodium alginate can be used as alkali metal salts. Ammonium alginate can also be used. The preparations can be produced for administration in the form of tablets, pills or powder and may contain known ingredients such as sodium bicarbonate or $Na_2HPO_4$ as well as binding agents for the production of tablets. Further additives which may be present in the appetite curbing compositions are flavorings, vitamins and sugar/fruit concentrates.

Generally speaking, the appetite curbing compositions according to the invention contain from 25% to 50% by weight of the alginate-diphosphonic acid preparation, with the balance up to 100% by weight being the other known ingredients and/or additives mentioned above which constitute an inert nontoxic pharmacologically acceptable carrier.

The appetite curbing compositions are administered orally to warm-blooded animals in units which contain an anoretically effective amount, or about 15 to 70 mg/kg of body weight (preferably 25 to 50 mg/kg of body weight), of the alginic-diphosphonic acid combination. These dosage units can be in the form of tablets, pills or powders and are conveniently administered by dissolving the tablets, pills or powders of the combination in a suitable liquid medium such as water, milk, fruit juice or a carbonated beverage. The liquid medium contains from 0.5% to 5% by weight of the appetite curbing composition, and can be consumed by drinking.

The appetite curbing preparations of the present invention have the advantage of preventing precipitation or excessive sequestering of calcium ions. The ease of digestibility of the anoretic agent is greatly increased, even for sensitive persons.

The following examples illustrate the present invention without limiting it in any manner.

EXAMPLE 1

In order to test the activity of the compositions containing compounds which might be effective as precipitation inhibitors, the following experiments were carried out. 600 mg of sodium alginate was slowly stirred into 50 ml of a solution of sodium bicarbonate ($Na_2HPO_4$) containing the inhibitor stated in Table I. After filling up to the final volume, the following concentrations were obtained per liter of alginate solution:

6 gm of sodium alginate
0.075 gm of precipitation inhibitor
2 gm of $HCO_3^-$ ions
0.1 gm of $HPO_4^-$ ions The above concentrations of bicarbonate and hydrogen phosphate ions were approximately equivalent to the inorganic components of intestinal juice. The solution had a pH of 8. As soon as the sodium alginate had homogeneously dissolved, 50 ml of 40° dH (German hardness) hard water was added, so that the solution had a calcium hardness of 20° dH. The precipitation of calcium alginate became apparent through gelling or clotting, which could readily be observed by means of deposits on the walls of the container when the sample was shaken.

A control sample of the alginic compound was also mixed with the bicarbonate-hydrogen phosphate solution. The results of the control test together with the results of the test with a composition of the invention are reported in Table I. The results of the same tests with comparative precipitation inhibitors are reported in Table II. The comparative tests clearly indicate that the desired results are not achieved with other prior art compounds, even though these do in part have a very similar sequestering effect.

Table I

| Precipitation Inhibitor | Results |
|---|---|
| None (control) | Strong to very strong gelation |
| 1,1-Diphosphonopropane-2,3-dicarboxylic acid | Weak gelation |

Table II

| Precipitation Inhibitors (Comparative) | Results |
|---|---|
| Methylenediphosphonic acid | Strong to medium strong gelation |
| Ethane-1,1-diphosphonic acid | Strong to very strong gelation |
| Propane-1,2,3-triphosphonic acid | Strong gelation |
| Methylphosphonosuccinic acid | Very strong gelation |
| 2-Phosphonobutane-1,2,4-tricarboxylic acid | Medium strong gelation |
| Amino-tris-(methylene-phosphonic acid) | Strong to extremely strong gelation |
| Dimethylaminomethane-diphosphonic acid | Medium strong to strong gelation |
| Aminoacetic acid-N,N-dimethylene-phosphonic acid | Very strong gelation |
| Chlorobenzyl-diphosphonic acid | Strong to very strong gelation |
| Ethylenediamine-tetrakis-(methylene-phosphonic acid) | Strong to very strong gelation |
| Hexamethylenediamine-tetrakis-(methylene-phosphonic acid) | Strong to very strong gelation |
| Cyclohexanehexa-carboxylic acid | Medium strong to strong gelation |

EXAMPLE 2

A preparation which was suitable as an appetite curbing agent was prepared from the following composition by weight:
64.5% sugar/fruit concentrate
35% sodium alginate
0.5% of the diphosphonic acid of Example 1
in the form of the sodium salt.

Approximately 6 gm of the anoretic preparation was placed in a dry glass and filled up with 200 gm of cold water while being stirred. The drink was imbibed approximately 15 minutes before the reduced meals.

Although the present invention has been disclosed in connection with a few preferred embodiments thereof, variations and modifications may be resorted to by those skilled in the art without departing from the principles of the new invention. All of these variations and modifications are considered to be within the true spirit and scope of the present invention as disclosed in the foregoing description and defined by the appended claims.

We claim:

1. An appetite curbing composition for warm-blooded animals comprising
   (A) an alginic compound selected from the group consisting of alginic acid and the nontoxic pharmacologically acceptable water-soluble salts thereof, and
   (B) a substoichiometric amount based on the calcium required to gel said alginic compound of a diphosphonic compound having the formula:

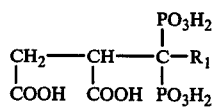

wherein $R_1$ is selected from the group consisting of hydrogen and methyl; or the nontoxic pharmacologically acceptable water-soluble salts thereof, the weight of said diphosphonic compound being 0.5% to 2% of the weight of said alginic compound and the amount of said diphosphonic compound being sufficient to inhibit precipitation of calcium alginate when said alginate is administered to animals.

2. A composition according to claim 1 wherein $R_1$ is hydrogen.

3. A composition according to claim 1 wherein $R_1$ is methyl.

4. A composition according to claim 1 wherein the diphosphonic compound is a 1,1-diphosphonopropane-2,3-dicarboxylic acid salt.

5. A composition according to claim 1 in which said alginic and diphosphonic compounds are present as partial salts which produce a pH in the range of 6 to 8.5 when dissolved in water.

6. A composition according to claim 1 wherein said salts are selected from the group consisting of the alkali metal, magnesium, ammonium and loweralkanol ammonium salts, and mixtures thereof.

7. A composition according to claim 1 in unit dose pill form.

8. An aqueous solution containing 0.5% to 5% by weight of the composition of claim 1.

9. An appetite curbing composition for a warm-blooded animal in the form of a tablet, pill or powder consisting essentially of from 25% to 50% by weight of the appetite curbing composition of claim 1, and from 50% to 75% by weight of a nontoxic pharmacologically acceptable carrier therefor.

10. A method for curbing the appetite of a warm-blooded animal comprising orally administering to said animal an anoretically effective amount of the appetite curbing composition of claim 1.

11. The method according to claim 10 wherein said anoretically effective amount is from 15 to 70 mg/kg of the weight of said animal.

12. The method according to claim 10 wherein said anoretically effective amount is from 25 to 50 mg/kg of the weight of said animal.

* * * * *